(12) United States Patent
Kang et al.

(10) Patent No.: US 10,258,438 B2
(45) Date of Patent: Apr. 16, 2019

(54) ORAL AUTOMATIC SCANNER

(71) Applicants: XYZPRINTING, INC., New Taipei (TW); KINPO ELECTRONICS, INC., New Taipei (TW)

(72) Inventors: Hung-Peng Kang, New Taipei (TW); Ming-Hsiung Ding, New Taipei (TW); Tsung-Hua Kuo, New Taipei (TW)

(73) Assignees: XYZPRINTING, INC., New Taipei (TW); KINPO ELECTRONICS, INC., New Taipei (TW)

( * ) Notice: Subject to any disclaimer, the term of this patent is extended or adjusted under 35 U.S.C. 154(b) by 18 days.

(21) Appl. No.: 15/660,952

(22) Filed: Jul. 27, 2017

(65) Prior Publication Data

US 2018/0344436 A1    Dec. 6, 2018

(30) Foreign Application Priority Data

May 31, 2017  (CN) .......................... 2017 1 0399539

(51) Int. Cl.
*A61C 9/00* (2006.01)
*A61B 1/00* (2006.01)
(Continued)

(52) U.S. Cl.
CPC .......... *A61C 9/008* (2013.01); *A61B 1/00009* (2013.01); *A61B 1/0016* (2013.01); *A61B 1/00172* (2013.01); *A61B 1/04* (2013.01); *A61B 1/05* (2013.01); *A61B 1/24* (2013.01); *A61B 5/0062* (2013.01); *A61B 5/0088* (2013.01); *A61C 1/0015* (2013.01); *A61C 9/004* (2013.01);
(Continued)

(58) Field of Classification Search
CPC ..... A61C 9/008; A61C 1/0015; A61C 9/0006; A61C 9/0053; A61B 1/04; A61B 1/24; A61B 1/00009; H04N 7/185
See application file for complete search history.

(56) References Cited

U.S. PATENT DOCUMENTS

| 2002/0055082 A1 | 5/2002 | Durbin et al. |
| 2013/0209954 A1* | 8/2013 | Prakash ............... A61B 1/0005 433/29 |

(Continued)

FOREIGN PATENT DOCUMENTS

| JP | 2012125455 A | 7/2012 |
| WO | 2017029670 A1 | 2/2017 |

OTHER PUBLICATIONS

Search Report dated Jan. 30, 2018 of the corresponding European patent application No. 17183081.3.

*Primary Examiner* — Marnie A Matt
(74) *Attorney, Agent, or Firm* — Chun-Ming Shih; HDLS IPR Services

(57) ABSTRACT

An automotive intraoral scanner applied in a mouth includes a biting piece, a track piece and at least one mobile image processing set. The biting piece is sandwiched between two rows of teeth. The track piece is installed in the biting piece and disposed corresponding to the rows of teeth, and a shape of the track piece is similar to a shape of the rows of teeth. The mobile image processing set is installed on the track piece and moved along the track piece, and the mobile image processing set is disposed corresponding to the rows of teeth. Therefore, the automotive intraoral scanner has advantages of easy operation.

10 Claims, 10 Drawing Sheets

(51) Int. Cl.
  *A61C 1/00*   (2006.01)
  *H04N 7/18*   (2006.01)
  *A61B 5/00*   (2006.01)
  *A61B 1/24*   (2006.01)
  *A61B 1/05*   (2006.01)
  *A61B 1/04*   (2006.01)

(52) U.S. Cl.
  CPC .......... *A61C 9/0006* (2013.01); *A61C 9/0053* (2013.01); *H04N 7/185* (2013.01); *A61B 1/00029* (2013.01); *A61B 1/00032* (2013.01); *A61B 2562/0233* (2013.01)

(56) References Cited

U.S. PATENT DOCUMENTS

| | | | | |
|---|---|---|---|---|
| 2014/0372084 | A1* | 12/2014 | Cowburn | A61C 9/0053 703/1 |
| 2015/0118638 | A1* | 4/2015 | Cowburn | A61C 9/0006 433/29 |
| 2015/0182299 | A1* | 7/2015 | Koubi | A61B 5/0088 433/27 |
| 2015/0209118 | A1* | 7/2015 | Kopelman | A61C 9/0053 433/25 |
| 2016/0324442 | A1* | 11/2016 | Zdeblick | A61B 5/073 |
| 2016/0338804 | A1* | 11/2016 | Kim | A61C 9/0053 |
| 2017/0086943 | A1* | 3/2017 | Mah | A61B 5/0022 |

\* cited by examiner

ORAL AUTOMATIC SCANNER

BACKGROUND OF THE INVENTION

Field of the Invention

The present invention generally relates to an oral medical instrument and, more particular to, an oral intraoral scanner device.

Description of Prior Art

In oral medical or oral health checkup, a handheld photography unit will be reached into mouth for capturing oral images as to facilitate observation of decayed or crooked teeth, and then a patient-specific oral model can be established.

However, images captured by the handheld photography unit will be displayed in tilt or upside down. Therefore, professional doctors or nursing staff rotates the handheld photography unit based on experience to get better images of observation. Hence a general beginner is not easy to operate the handheld photography unit by their own to get images of oral.

In view of the above drawbacks, the Inventor proposes the present invention based on his expert knowledge and elaborate researches in order to solve the problems of prior art.

SUMMARY OF THE INVENTION

Accordingly, an object of the present invention is to provide an automotive intraoral scanner, in which the shape of the track piece is similar to the shape of the row of teeth so that the mobile image processing set moves along the track piece as to replace procedures operated by professional doctors or nursing staff based on their experience. Therefore, the automotive intraoral scanner has advantages of easy operation.

In order to achieve the object mentioned above, the present invention provides an automotive intraoral scanner applied in a mouth, the mouth has an upper and a lower rows of teeth, the automotive intraoral scanner includes a biting piece disposed and sandwiched between the two rows of teeth. A track piece is installed in the biting piece and disposed corresponding to the rows of teeth, and a shape of the track piece is similar to a shape of the rows of teeth. And at least one mobile image processing set is installed on the track piece and moved along the track piece, wherein the mobile image processing set is disposed corresponding to the rows of teeth.

BRIEF DESCRIPTION OF DRAWING

The features of the invention believed to be novel are set forth with particularity in the appended claims. The invention itself, however, may be best understood by reference to the following detailed description of the invention, which describes a number of exemplary embodiments of the invention, taken in conjunction with the accompanying drawings, in which:

DETAILED DESCRIPTION OF THE PREFERRED EMBODIMENTS

In cooperation with attached drawings, the technical contents and detailed description of the invention are described thereinafter according to a number of preferable embodiments, being not used to limit its executing scope. Any equivalent variation and modification made according to appended claims is all covered by the claims claimed by the present invention.

Please refer to FIG. 1 to FIG. 4, the present invention provides a first embodiment of an automotive intraoral scanner. The automotive intraoral scanner 10 mainly includes a biting piece 1, a track piece 2 and one or a plurality of mobile image processing set 5.

Figure 1:
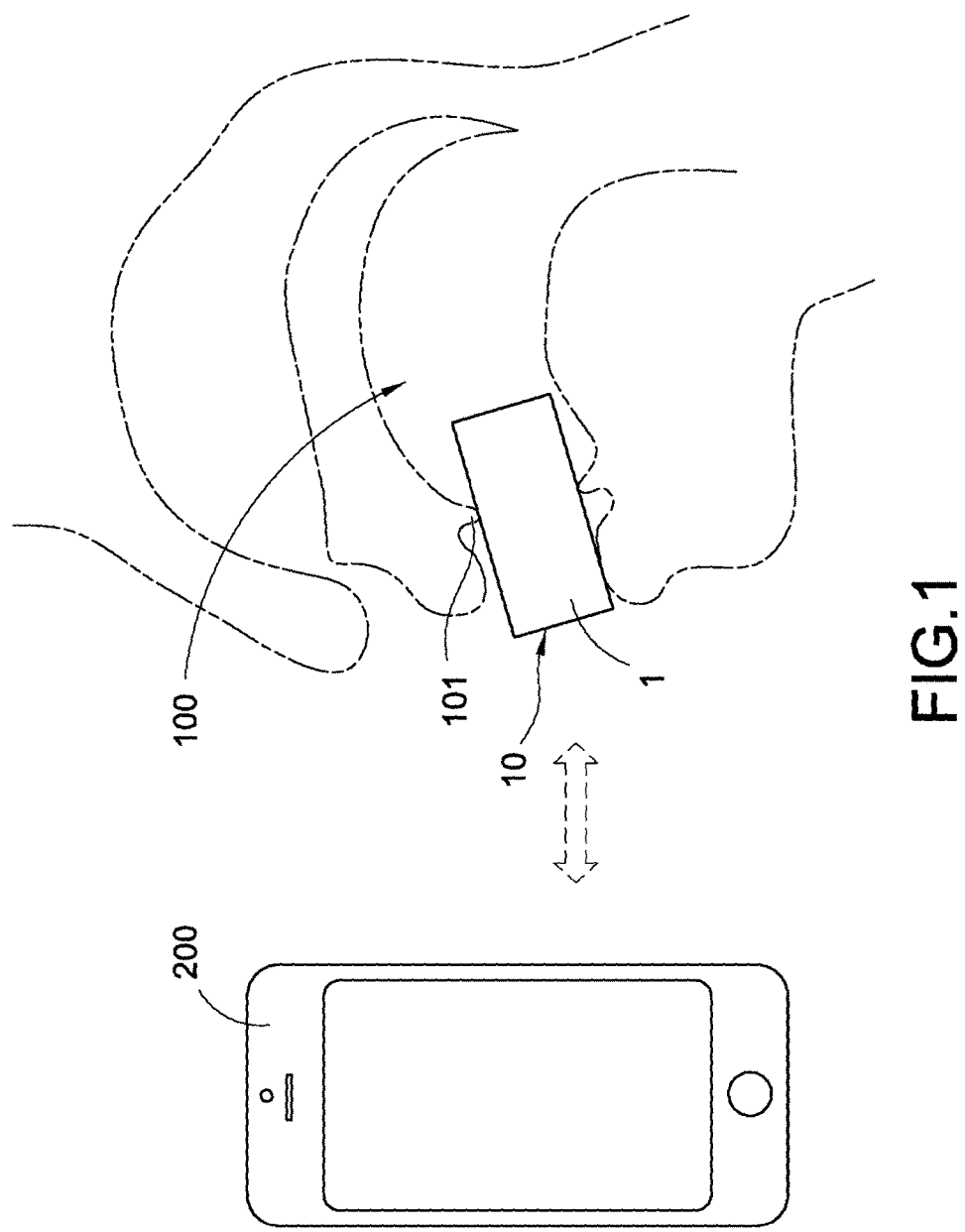
FIG. 1 is a schematic view showing an operating status of a first embodiment of an automotive intraoral scanner of the present invention.
Figure 3:
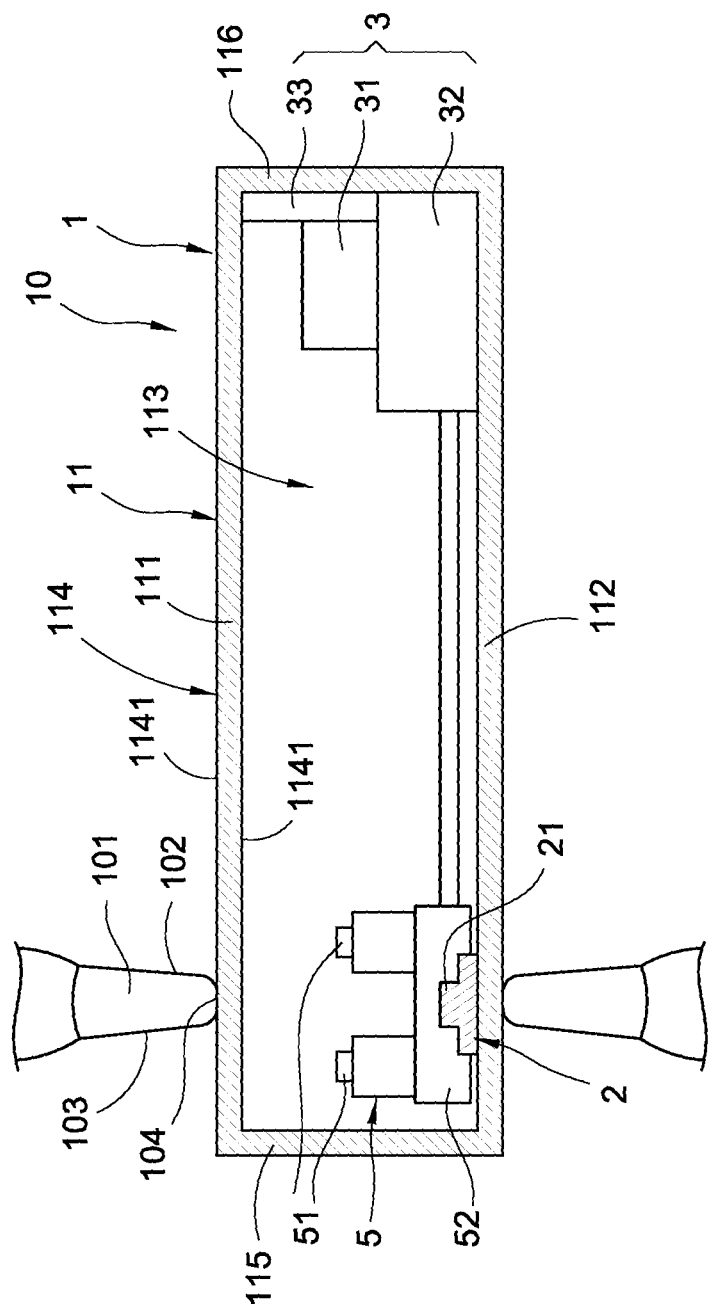
FIG. 3 is a cross sectional schematic view of a first embodiment of an automotive intraoral scanner of the present invention.

As shown in FIG. 1 and FIG. 3, the automotive intraoral scanner 1 is applied in a mouth 100. The mouth 100 has an upper and a lower rows of teeth 101, and each of the rows of teeth 101 has an inner tooth surface 102, an outer tooth surface 103 and a tooth end 104.

As shown in FIG. 1 to FIG. 4, the biting piece 1 is a transparent waterproof shell 11. The transparent waterproof shell 11 has a top 111, a bottom 112 and a cavity 113 therein, wherein at least one of the top 111 and the bottom 112 has a transparent wall 114, and the transparent wall 114 is disposed corresponding to the rows of teeth 101. In the present embodiment, the top 111 has a transparent wall 114, and the transparent wall 114 has two flat surfaces 1141 oppositely. In addition, the transparent waterproof shell 11 has disposed a U-shaped outer side wall 115 and an I-shaped outer side wall 116 oppositely. The U-shaped outer side wall 115 and the I-shaped outer side wall 116 are disposed at a left and a right sides of the transparent waterproof shell 11.

Figure 2:
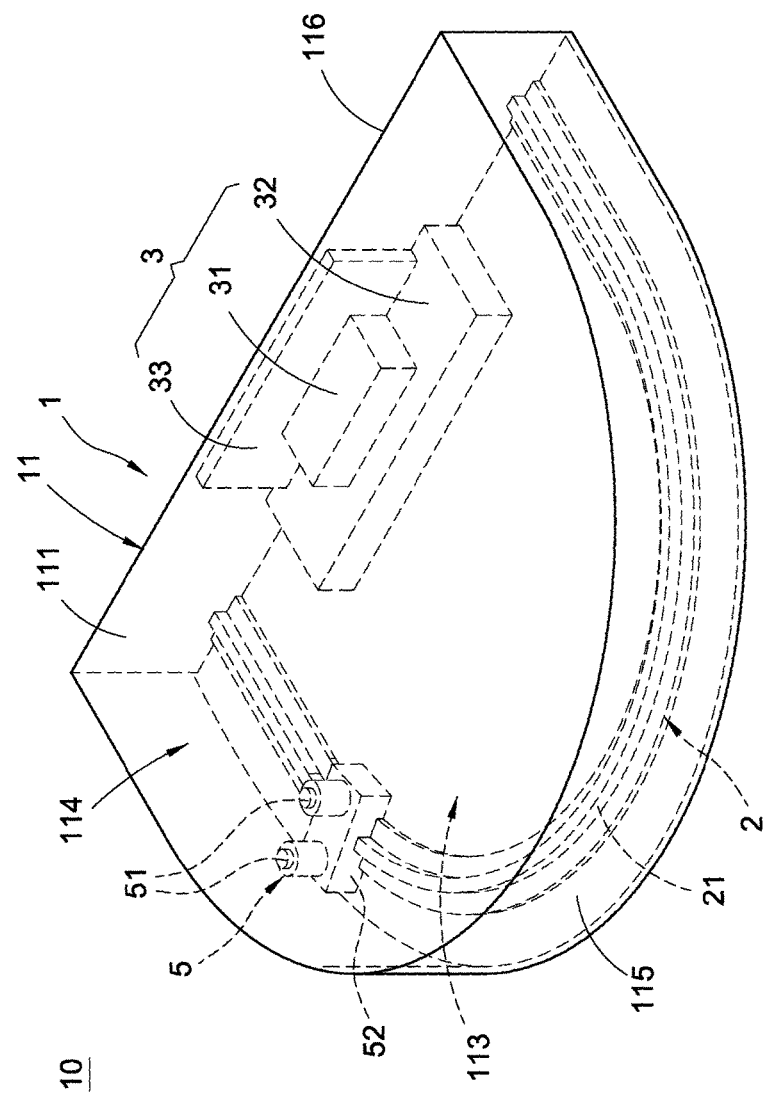
FIG. 2 is a perspective schematic view of a first embodiment of an automotive intraoral scanner of the present invention.
Figure 4:
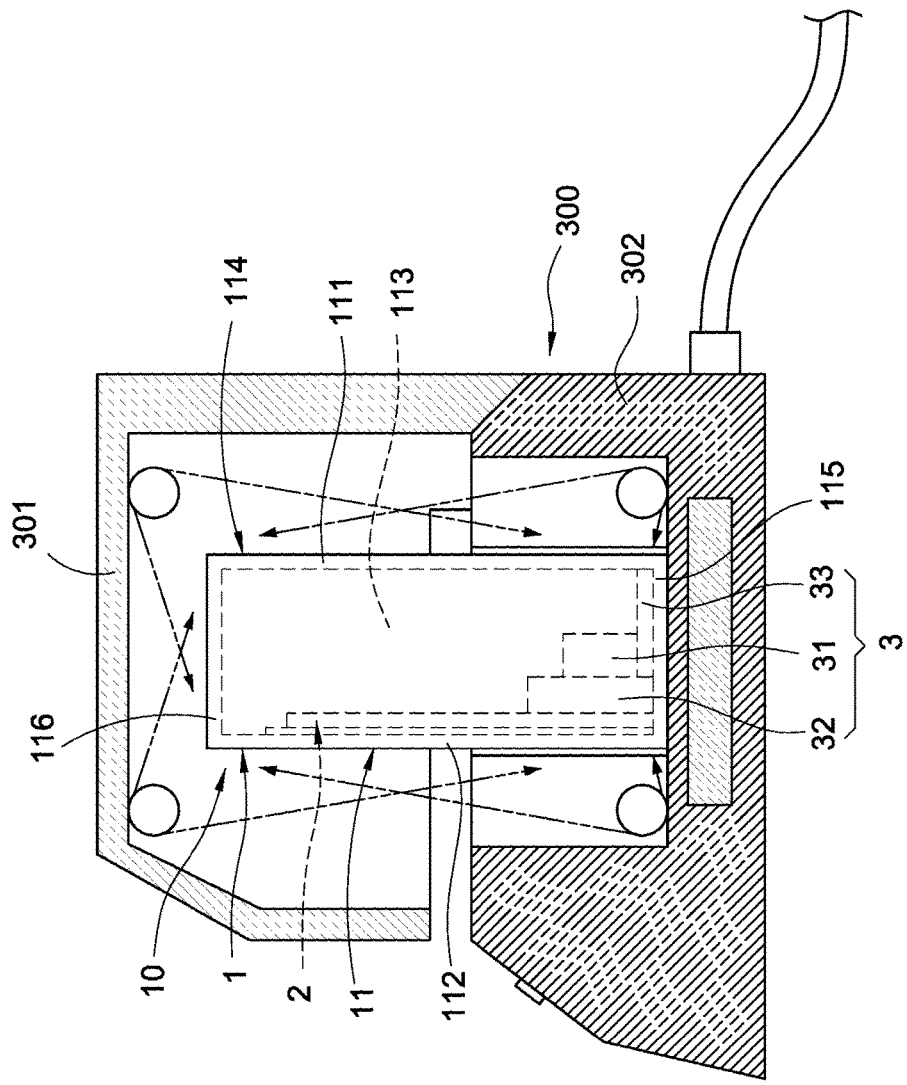
FIG. 4 is another schematic view showing an operating status of the first embodiment of an automotive intraoral scanner of the present invention.

As shown in FIG. 2 to FIG. 4, the track piece 2 is installed in the cavity 113 and disposed corresponding to the transparent wall 114, and a shape of the track piece 2 is similar to a shape of the row of teeth 101. In the present embodiment, the tooth row 101 is configured in a U shape so that the track piece 2 is a U-shaped path 21 disposed neighboring the U-shaped outer side wall 115.

As shown in FIG. 2 to FIG. 4, the automotive intraoral scanner 10 of the present embodiment further includes a control circuit module 3. The control circuit module 3 is installed in the cavity 113, and the control circuit module 3 comprises a circuit board 31, a battery 32 and a charge induction coil 33. The battery 32 and the charge induction coil 33 are electrically connected with the circuit board 31 separately. The circuit board 31, the battery 32 and the charge induction coil 33 are disposed adjacent to the I-shaped outer side wall 116 together.

Please refer to FIG. 2 to FIG. 3, one or a plurality of mobile image processing sets 5 are accommodated in the cavity 113. One or a plurality of mobile image processing sets 5 are installed on the track piece 2 and moved along the track piece 2, and the mobile image processing set 5 is disposed corresponding to the row of teeth 101.

The details are as follows. Each mobile image processing set 5 further includes a plurality of image processors 51 and a driver 52. The driver 52 is installed on the track piece 2 and moved along the track piece 2. The image processors 51 are fixed on the driver 52 and moved with the driver 52. Each image processor 51 is a camera or a 3D scanner, wherein the driver 52 is, but not limited to, a driving motor.

Moreover, each image processor 51 and the driver 52 are electrically connected with the control circuit module 3 separately. That is, each image processor 51 and the driver 52 are electrically connected with the circuit board 31 separately for the driver 52 can drive the mobile image processing set 5 moving along the track piece 2. The mobile image processing set 5 is disposed corresponding to the row of teeth 101 and captures images through the transparent wall 114.

Each image processing set 5 of the present embodiment comprises two image processors 51. One of the image processors 51 is disposed corresponding to the inner teeth surface 102 and the tooth end 104, and another image processor 51 is disposed corresponding to the outer tooth surface 103 and the tooth end 104 as to obtain images of the rows of teeth 101, wherein each image processor 51 is a camera or a 3D scanner with structures for generating light.

As shown in FIG. 1 to FIG. 3, the combination of the automotive intraoral scanner 10 of the present invention is implemented by utilizing a biting piece 2 disposed and sandwiched between the two rows of teeth 101. The track piece 2 is installed in the biting piece 1 and disposed corresponding to the rows of teeth 101, and a shape of the track piece 2 is similar to a shape of the rows of teeth 101. The mobile image processing set 5 is installed on the track piece 2 and moved along the track piece 2, and the deposition of the mobile image processing set 5 is corresponding to the row of teeth 101.

As shown in FIG. 1 to FIG. 4, they show operating status of an automotive intraoral scanner of the present invention. Firstly, the automotive intraoral scanner 10 is disposed in a mouth 100, and then a mobile phone 200, a tablet PC or a computer etc. is used to active the automotive intraoral scanner 10 and receives 3D images of the mouth 100 therein. Furthermore, as the shape of the track piece 2 is similar to the shape of the row of teeth 101, the mobile image processing set 5 moves along the track piece 2 which can replace prior procedures of rotating the photography unit by professional doctors or nursing staff base on their experience. Therefore, users can easily obtain the 3D image of the mouth 100 therein without complex operation. Thus the automotive intraoral scanner 10 has advantage of easy operation.

In addition, as shown in FIG. 3, the transparent wall 114 of the present invention has two flat surfaces 1141 oppositely. The mobile image processing set 5 utilizes two image processors 51 to capture 3D images of the inner and outer rows of teeth 101 clearly by disposing one image processor 51 facing the inner tooth surface 102 and the tooth end 104 and another image processor 51 facing the outer tooth surface 103 and the tooth end 104.

Moreover, as in FIG. 4, the automotive intraoral scanner 10 can be used on a charging stand 300. The charging stand 300 has an upper light sterilization seat 301 and a lower inductive charge seat 302. The upper light sterilization seat 301 generates a UV LED sterilization to sterilize the transparent waterproof shell 11, and the lower inductive charge seat 302 can charge the battery 32 through the charge induction coil 33.

Figure 5:
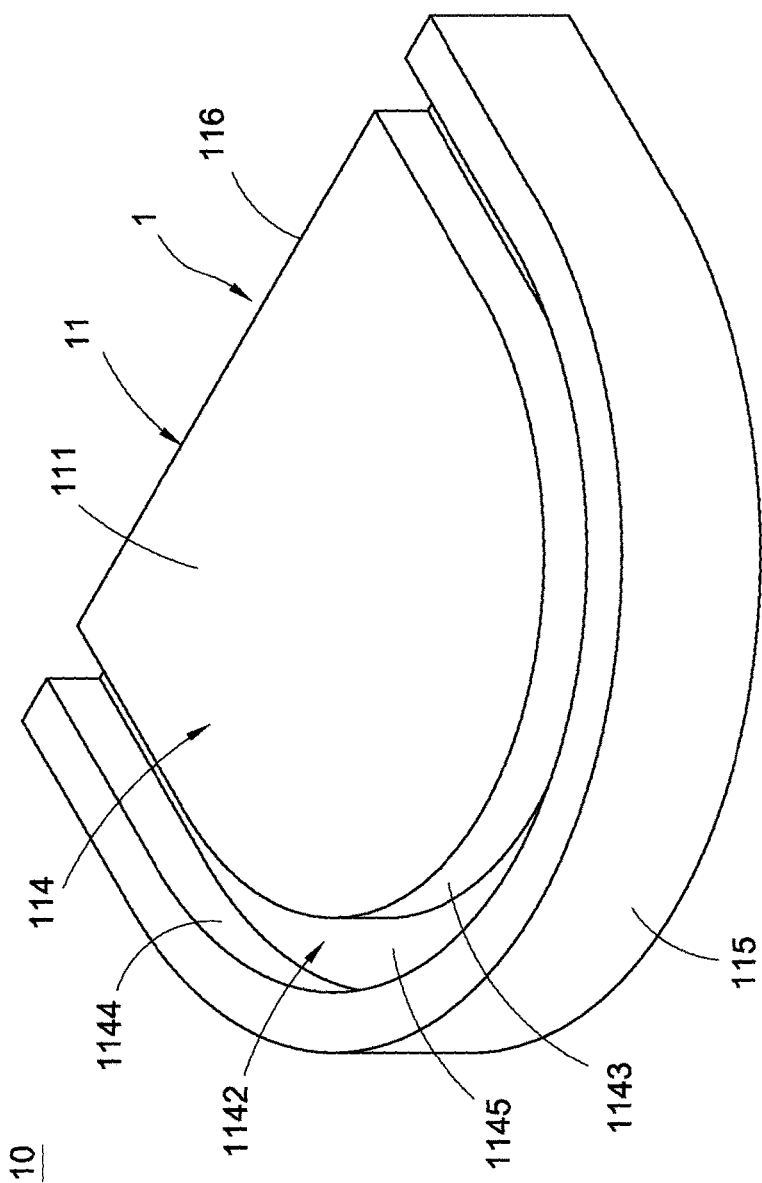
FIG. 5 is a perspective schematic view of a second embodiment of an automotive intraoral scanner of the present invention.
Figure 6:
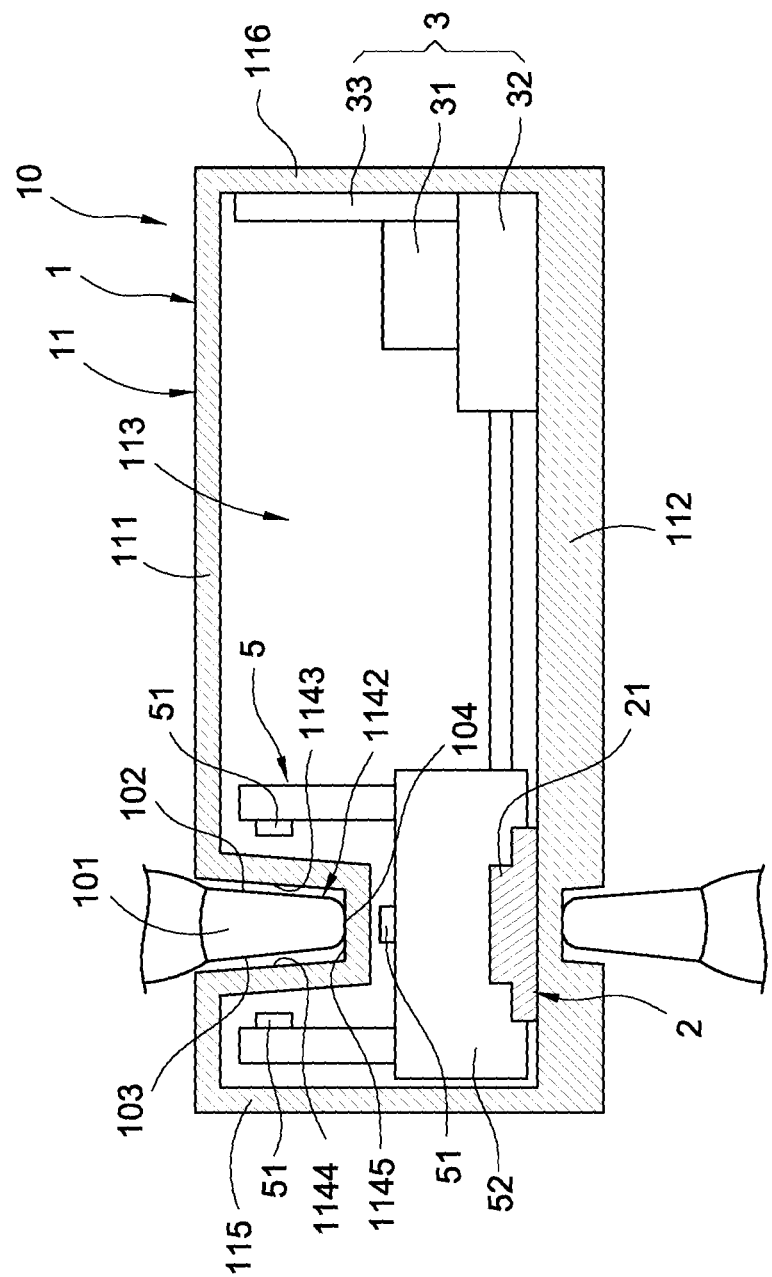
FIG. 6 is a cross sectional schematic view of a second embodiment of an automotive intraoral scanner of the present invention.

Please refer to FIG. 5 to FIG. 6; they depict a second embodiment of the automotive intraoral scanner 10 of the present invention. The second embodiment is substantially the same as the first embodiment. The second embodiment differs from the first embodiment in that the transparent wall 114 is provided with a hollow trough 1142.

Further description is as follows. The transparent wall 114 has a hollow trough 1142. The shape of the hollow trough 1142 is similar to the shape of the row of teeth 101 so that the row of teeth 101 can be accommodated in the hollow trough 1142. The hollow trough 1142 has a first inner side surface 1143, a second inner side surface 1144 and an inner bottom surface 1145 therein. The inner tooth surface 102 is adjacent to the first inner side surface 1143, the outer tooth surface 103 is adjacent to the second inner side surface 1144, and the tooth end 104 is adjacent to the inner bottom surface 1145. Each mobile image processing set 5 comprises three image processors 51, wherein one image processor 51 is disposed corresponding to the first inner side surface 1143, another image processor 51 is disposed corresponding to inner side surface 1144, and the rest of the image processors 51 is disposed corresponding to the inner bottom surface 1145. Thus, clear 3D images of the inner and outer rows of teeth 101 can be captured.

Figure 7:
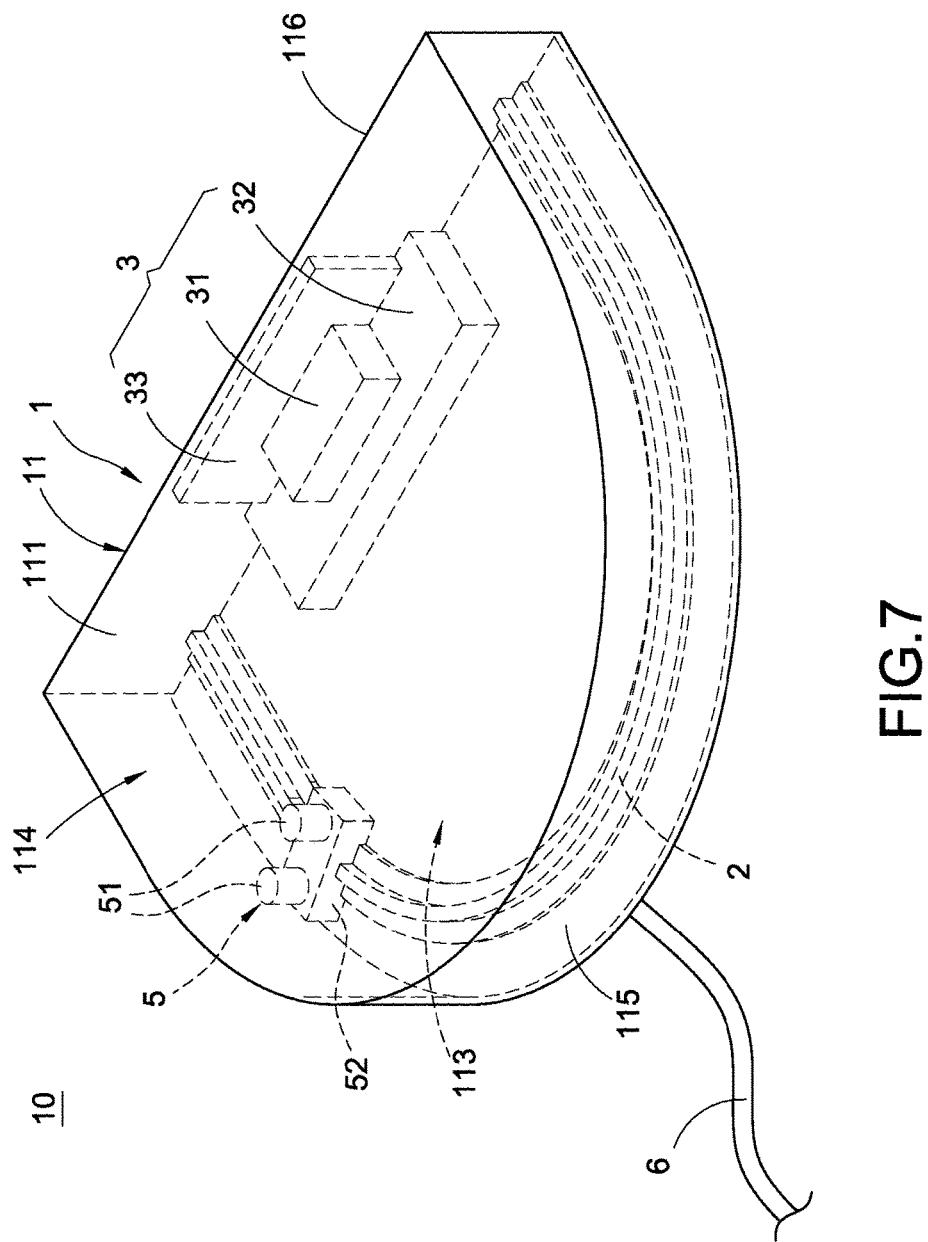
FIG. 7 is a perspective schematic view of a third embodiment of an automotive intraoral scanner of the present invention.

Please refer to FIG. 7, it depicts a third embodiment of the automotive intraoral scanner of the present invention. The third embodiment is substantially the same as the first embodiment, but the third embodiment differs from the first embodiment in that the automotive intraoral scanner 10 further comprises a power cable 6.

The details are as follows. The power cable 6 is installed outside the transparent waterproof shell 11 and electrically connected with circuit board 31. The power cable 6 can be plugged on the outside power socket for charging the battery 32.

Figure 8:
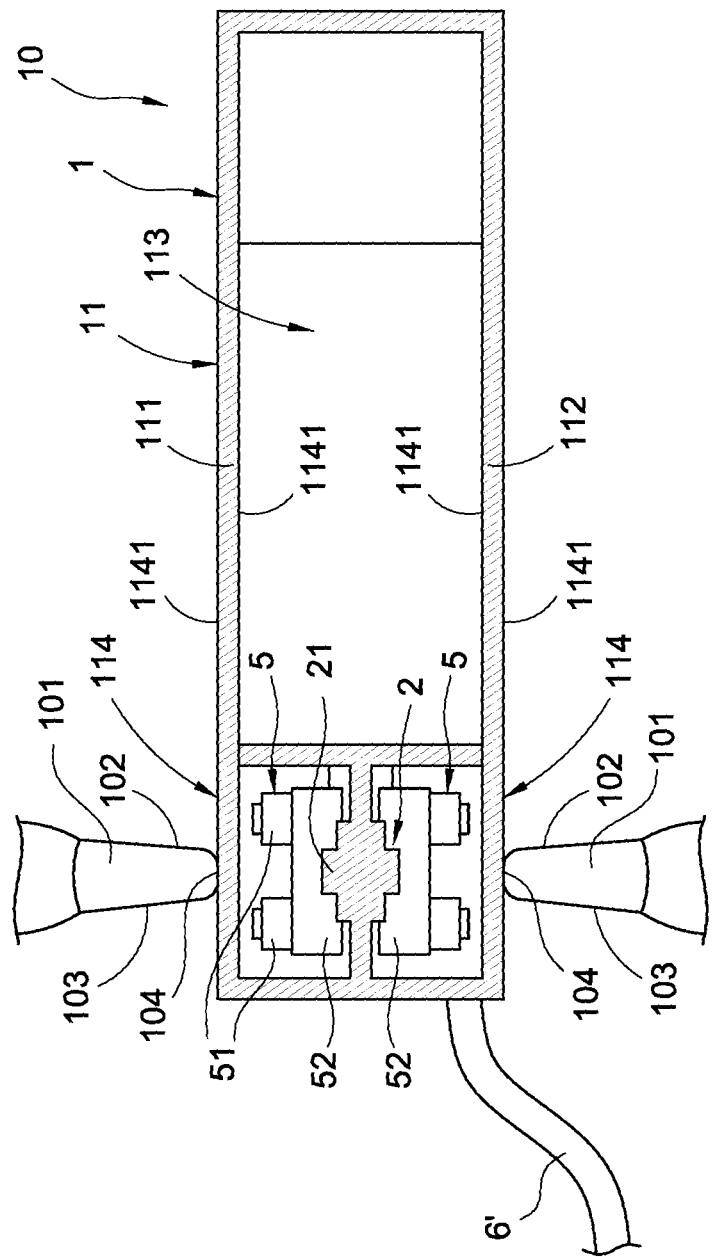
FIG. 8 is a cross sectional schematic view of a fourth embodiment of an automotive intraoral scanner of the present invention.
Figure 9:
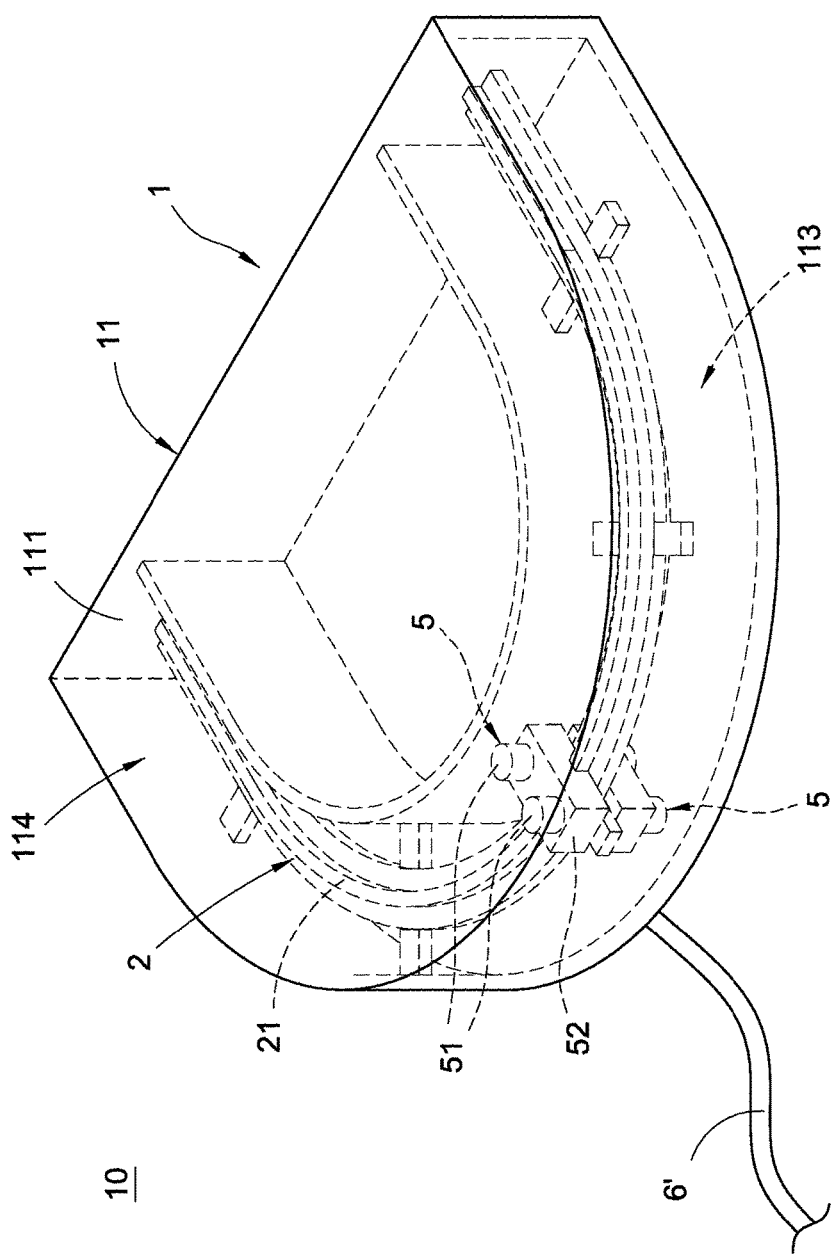
FIG. 9 is a perspective schematic view of a fourth embodiment of an automotive intraoral scanner of the present invention.

Please refer to FIG. 8 and FIG. 9, they depict a fourth embodiment of the automotive intraoral scanner 10 of the present invention. The fourth embodiment is substantially the same as the first and the second embodiments, but the fourth embodiment differs from the first and second embodiments in that the quantity of the transparent wall 114 and the mobile image processing set 5 is two separately.

Further description is as follows. In the present embodiment, two transparent walls 114 are formed at the top 111 and the bottom 112 separately. The track piece 2 is disposed corresponding to the two transparent walls 114, and the driver 52 drives two mobile image processing sets 5 moved along an upper and a lower sides of the track piece 2. Thus 3D images of the upper and lower rows of teeth 101 of mouth can be obtained when the mobile image processing set 5 finish the moving along the track piece 2.

Moreover, the two transparent walls 114 of the present has two flat surfaces 1141 oppositely (as shown in the first embodiment) to obtain 3D images of the upper and lower rows of teeth 101 and achieve the same function and effect as the first embodiment; or the two transparent walls 114 of the present has a hollow trough 1142 separately (as shown in the second embodiment) to obtain the 3D images of the upper and the lower lows of teeth 101 as to reach the same function and effect of the second embodiment.

Besides, the automotive intraoral scanner 10 further includes a power cable 6'. The power cable 6' is installed in the transparent waterproof shell 11 outside and electrically connected with the driver 52 and the mobile image processing set 5. The power cable 6' can be plugged on the outside power socket for charging the driver 52 and the mobile image processing set 5.

Figure 10:
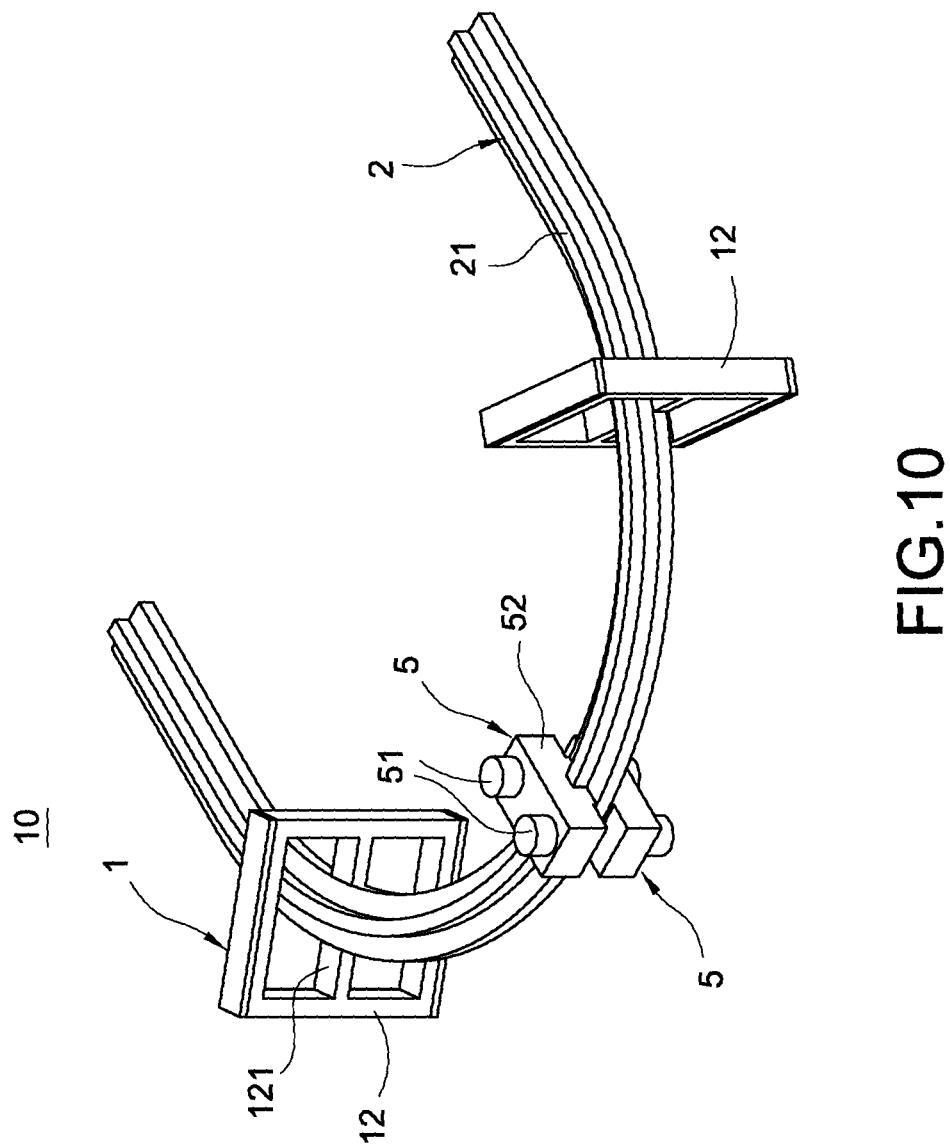
FIG. 10 is a perspective schematic view of a fifth embodiment of an automotive intraoral scanner of the present invention.

Please refer to FIG. 10, it depicts a fifth embodiment of the automotive intraoral scanner 10 of the present invention. The fifth embodiment is substantially the same as the first embodiment, but the fifth embodiment differs from the first and second embodiments in that structures of the biting piece 1.

The details are as follows. The biting piece 1 is a plurality of top gear racks 12. Each of the top gear racks 12 has a connecting rod 121 therein, and the track piece 2 is connected across the connecting rods 121. Thereby, the automotive intraoral scanner 10 is disposed in mouth 100, and two rows of teeth 101 are clamped corresponding to the plural top gear racks 12. Then followed by the same procedure as that shown in the first embodiment, the mobile image processing set 5 is moved along the biting piece 2 to obtain 3D images of the mouth 100 therein for reaching the same function and effect as the first embodiment.

Although the present invention has been described with reference to the preferred embodiment thereof, it will be understood that the invention is not limited to the details thereof. Various substitutions and improvements have been suggested in the foregoing description, and others will occur to those of ordinary skill in the art. Therefore, all such substitutions and improvements are intended to be embraced within the scope of the invention as defined in the appended claims.

What is claimed is:

1. An automotive intraoral scanner applied in a mouth, the mouth having an upper and a lower row of teeth, the automotive intraoral scanner including:
   a bite piece disposed and sandwiched between the two rows of teeth, wherein the bite piece is a transparent waterproof shell, and the transparent waterproof shell has a cavity therein, a U-shaped outer side wall and an I-shaped outer side wall disposed opposite to each other;
   a track piece installed in the bite piece and disposed corresponding to the rows of teeth; a shape of the track piece being the same as a shape of the rows of teeth, and the track piece is a U-shaped path disposed neighboring the U-shaped outer side wall;
   at least one mobile image processing set installed on the track piece and moved along the track piece, wherein the mobile image processing set is disposed corresponding to the rows of teeth; and
   a control circuit module, wherein the control circuit module is installed in the cavity, the control circuit module comprises a circuit board and a battery electrically connected with each other, and the mobile image processing set is electrically connected with the circuit board; the control circuit module further includes a charge induction coil, and the charge induction coil is electrically connected with the circuit board; the circuit board, the battery and the charge induction coil are disposed adjacent to the I-shaped outer side wall together.

2. The automotive intraoral scanner according to claim 1, wherein the transparent waterproof shell has a top and a bottom; at least one of the top and the bottom has a transparent wall, and the transparent wall is disposed corresponding to the rows of teeth; the track piece is installed in the cavity and corresponds with the transparent wall.

3. The automotive intraoral scanner according to claim 2, wherein quantities of the transparent wall and the mobile image processing set are two; two transparent walls are formed at the top and the bottom separately; the track piece is disposed corresponding to the two transparent walls, and two mobile image processing sets are moved along an upper and a lower side of the track piece.

4. The automotive intraoral scanner according to claim 2, wherein the transparent wall has two opposing flat surfaces, and the row of teeth has an inner tooth surface, an outer tooth surface and a tooth end; each mobile image processing set comprises two image processors, and one of the two image processors is disposed corresponding to the inner teeth surface and the tooth end, and the other one of the two image processors is disposed corresponding to the outer tooth surface and the tooth end, wherein each of the image processors is a camera or a 3D scanner.

5. The automotive intraoral scanner according to claim 2, wherein the transparent wall has a hollow trough, and a shape of the hollow trough is the same as a shape of the row of the teeth; the row of the teeth is accommodated in the hollow trough, and the hollow trough has a first inner side surface, a second inner side surface and an inner bottom surface therein; each mobile image processing set comprises three image processors, and one of the three image processors is disposed corresponding to the first inner side surface, another one of the three image processors is disposed corresponding to the second inner side surface, and still another one of the three image processors is disposed corresponding to the inner bottom surface, wherein each of the three image processors is a camera or a 3D scanner.

6. The automotive intraoral scanner according to claim 1, further including a power cable, and the power cable is installed outside the transparent waterproof shell and electrically connected with the circuit board.

7. The automotive intraoral scanner according to claim 1, further including a power cable, and the power cable is installed outside the transparent waterproof shell and electrically connected with the mobile image processing set.

8. The automotive intraoral scanner according to claim 1, wherein the bite piece is a plurality of top gear racks, and each of the top gear racks has a connecting rod therein, and the track piece is connected across the connecting rods.

9. The automotive intraoral scanner according to claim 1, wherein a quantity of the mobile image processing set is two, two mobile image processing sets are moved along an upper and a lower sides of the track piece respectively.

10. The automotive intraoral scanner according to claim 2, wherein the mobile image processing set further includes a plurality of image processors and a driver; the driver is installed on the track piece and moved along the track piece; the image processors are fixed on the driver and moved with the driver, and the image processor is a camera or a 3D scanner.

* * * * *

UNITED STATES PATENT AND TRADEMARK OFFICE
CERTIFICATE OF CORRECTION

PATENT NO.        : 10,258,438 B2
APPLICATION NO.   : 15/660952
DATED             : April 16, 2019
INVENTOR(S)       : Hung-Peng Kang, Ming-Hsiung Ding and Tsung-Hua Kuo Page 1 of 1

It is certified that error appears in the above-identified patent and that said Letters Patent is hereby corrected as shown below:

On the Title Page

Item (54) Invention Title:
Change "Oral automatic scanner" to --AUTOMOTIVE INTRAORAL SCANNER--

Signed and Sealed this
Twentieth Day of August, 2019

Andrei Iancu
*Director of the United States Patent and Trademark Office*